United States Patent [19]

Ison

[11] Patent Number: Plant 7,295

[45] Date of Patent: Aug. 14, 1990

[54] AFRICAN QUEEN

[76] Inventor: William G. Ison, Rte. 1, Box 19, Hwy. 19, Brooks, Ga. 30205

[21] Appl. No.: 166,250

[22] Filed: Mar. 10, 1988

[51] Int. Cl.[5] ..... A01H 5/00

[52] U.S. Cl. ..... Plt./47

[58] Field of Search ..... Plt./47

*Primary Examiner*—Robert E. Bagwill

*Attorney, Agent, or Firm*—Eugene T. Holmes

[57] ABSTRACT

A cross between the female variety Sugargate and the pollen parent Dixieland to produce an improved variety of self-fertile muscadine grape.

1 Drawing Sheet

DESCRIPTION OF THE VARIETY

A cross between the female seed parent Sugargate and the pollen parent variety Dixieland.

The primary objective of the breeding was to produce an improved variety of muscadine grape, the fruit to be large, black, and characteristics to include even ripening, excellent taste, high sugar content, dry scar for longer shelf life, and the plant to be productive and vigorous.

In comparison with both the seed parent and the pollen parent, the new variety is similar in size to the seed parent and resembles in color the seed parent. The new variety is similar in excellent quality to the pollen parent, Dixieland which is outstanding. The fruit of this new variety contains an average 22% soluble solids. The parent seed variety is comparable in soluble solids while the pollen parent is lower. The present variety yields approximately 4 to 6 tons per acre of fruit in tests conducted at Ison's Nursery & Vineyards, Brooks, Ga. The taste of this new variety is outstanding, having the true muscadine taste, twangy, acid, but sweet. Ripens mid-season.

Asexual reproduction of the new variety either by softwood cuttings or by layering as performed at Brooks, Ga. shows that the foregoing characteristics and distinctions come true to form and are established and transmitted through succeeding propagations.

The accompanying photograph shows a typical specimen of the vegetative growth and fruit of the new variety when the fruit is ripe and ready for picking and as depicted in color as nearly true as it is reasonably possible to make the same in color illustration of the characters.

The following is a detailed description of the new variety:

Species: *Vitis rotundifolia.*
Type: Vine.

Seed variety: Variety Sugargate.
Pollen parent: Variety Dixieland.
Propagation: Holds its characteristics through succeeding propagation by either layering or by softwood cuttings.
Locality where grown: Brooks, Ga.
Fruit borne: Usually in clusters of 4 to 12 berries per cluster.
Fruit size: Large, 1 to 1⅛" diameter.
Fruit color: Black, Black Group 202A Fan 4, Royal Horticultural Society, London, England.
Sugar content: Average 22% Soluble solids.
Fruit shape: Round.
Seed: Average diameter ⅛", average seed per berry 2½.
Pulp: Color Greyed Green, 194A Fan 4 Royal Horticultural Society, Fan 4 London, England.
Consistency: Pulp is meaty, tender and juicy.
Skin: Medium thick.
Foliage: Leaf Color, Green Group 135D Fan 3 Royal Horticultural Society, London, England. Leaf size and shape similar to most muscadine varieties.
Reproductive organs: Pistillate-not self pollinating. Note: This is a Female variety which can be reproduced from cuttings, but when planted will not pollinate other varieties.
Growth habits: Very Vigorous, ripens uniform, very productive.vine requires support.
Canes: Small to Medium.
Maturity date: Usually ripens about Sept. 20 at Brooks, Ga.
Diseases: Disease resistant.

This description was made from a muscadine vine grown at Ison's Nursery & Vineyards, Brooks, Ga.

I claim:

1. The new and distinct variety of grape plant as described and illustrated.

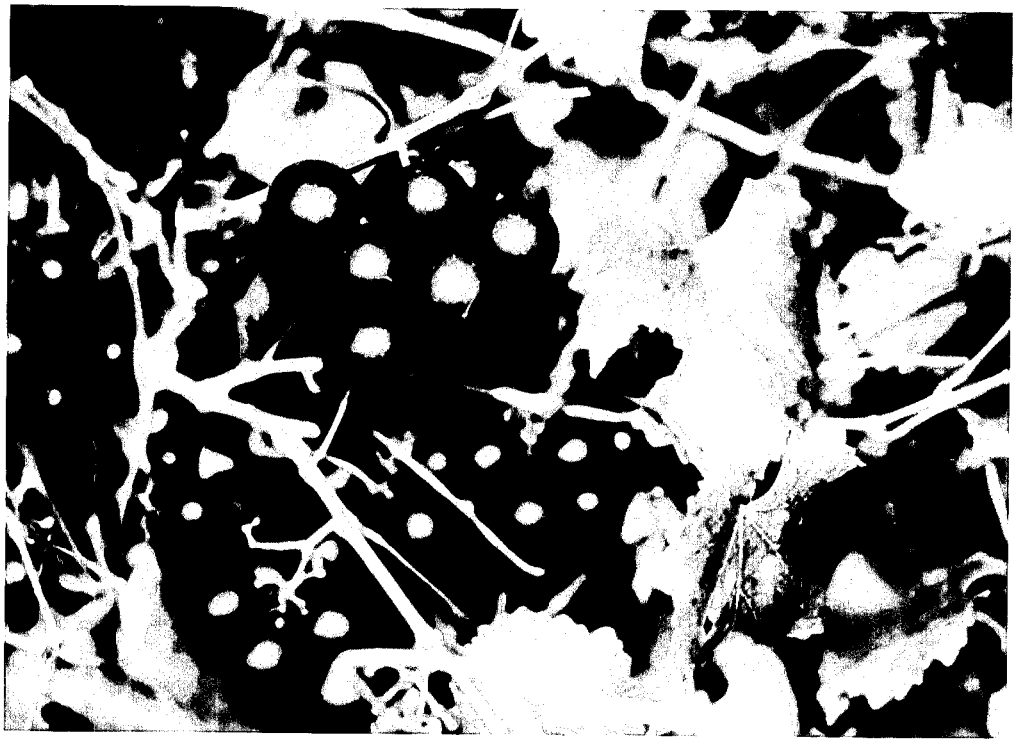

* * * * *